US006636031B1

United States Patent
Kenmochi et al.

(10) Patent No.: US 6,636,031 B1
(45) Date of Patent: Oct. 21, 2003

(54) METHOD AND DEVICE FOR DETECTING PINHOLES IN ORGANIC FILM ON CONCRETE SURFACE

(75) Inventors: Fukio Kenmochi, Kawasaki (JP); Takao Tsurudome, Kawasaki (JP); Masaaki Houki, Osaka (JP); Noboru Yamazaki, Osaka (JP)

(73) Assignees: Sanko Electronic Laboratory Co., Ltd., Kanagawa (JP); Shinko Electric & Instrumentation Co., Ltd, Osaka (JP)

( * ) Notice: Subject to any disclaimer, the term of this patent is extended or adjusted under 35 U.S.C. 154(b) by 0 days.

(21) Appl. No.: 09/679,899

(22) Filed: Oct. 5, 2000

(51) Int. Cl.⁷ .......................... G01R 1/04; G01R 27/08; G01N 27/00
(52) U.S. Cl. .................. 324/158.1; 324/557; 324/691
(58) Field of Search ................... 324/557, 558, 324/559, 691, 693, 707, 710, 718, 719, 514, 512, 71.1; 340/605; 73/40, 40.5 R, 40.5 A

(56) References Cited

U.S. PATENT DOCUMENTS

| | | | |
|---|---|---|---|
| 3,252,155 A | | 5/1966 | Surtees et al. |
| 3,810,007 A | * | 5/1974 | Wiseman et al. ............ 324/557 |
| 4,243,932 A | * | 1/1981 | Kakumoto et al. .......... 324/557 |
| 4,914,395 A | * | 4/1990 | Hamada ..................... 324/557 |
| 5,084,680 A | | 1/1992 | Mitchell et al. |
| 6,288,554 B1 | * | 9/2001 | Yasumoto .................... 324/558 |

FOREIGN PATENT DOCUMENTS

| | | | | |
|---|---|---|---|---|
| EP | 0245116 A2 | | 11/1987 | |
| JP | 05093702 A | * | 4/1993 | .............. 324/76.11 |
| JP | 10185852 A | * | 7/1998 | .......... G01N/27/20 |
| JP | 2000131261 A | * | 5/2000 | .......... G01N/27/20 |
| JP | 2001324407 A | * | 11/2001 | .......... G01N/27/92 |

* cited by examiner

Primary Examiner—Kamand Cuneo
Assistant Examiner—Jermele Hollington
(74) Attorney, Agent, or Firm—TraskBritt

(57) ABSTRACT

A technique for detecting whether or not a pinhole is present in an organic film on a concrete surface, by detecting the conductivity of the concrete in advance. In the bottom portion of a measuring means body having a high-frequency oscillator accommodated therein, there are disposed electrodes which are insulated from each other through an insulating plate. Two electrodes are provided in parallel and are placed in contact with the surface of the lining film coating the surface of the concrete body. Thus, the electrodes are held in contact with the surface of the lining film, and a high-frequency signal is fed from the high-frequency oscillator to between the electrodes. Then, by detecting the specific dielectric, constant of the concrete body or the base body indirectly from the surface layer of the organic film without breaking the organic film formed on the surface to expose the surface of the concrete body, the conductivity of the concrete can be examined from the correlation between the specific dielectric constant and the water content, as investigated in advance, and the correlation between the water content and the electric resistance.

4 Claims, 5 Drawing Sheets

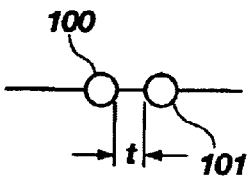
FIG. 1A
(PRIOR ART)
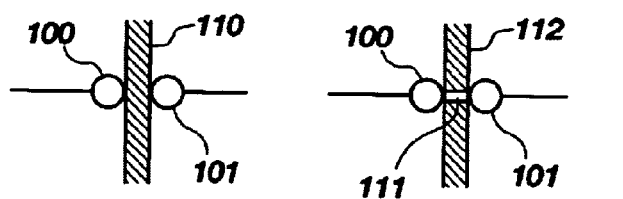
FIG. 1B
(PRIOR ART)
FIG. 1C
(PRIOR ART)
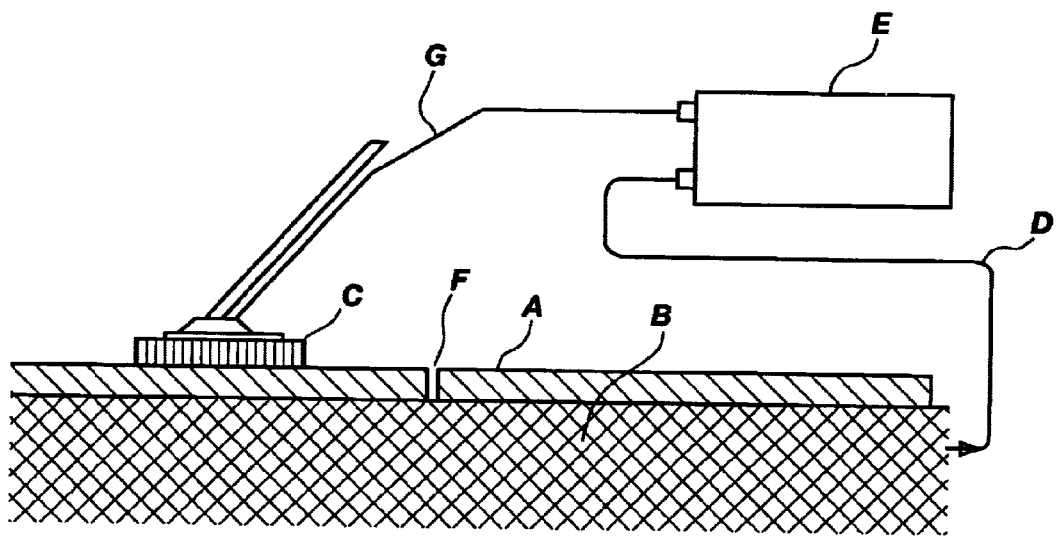
FIG. 2
(PRIOR ART)

METHOD AND DEVICE FOR DETECTING PINHOLES IN ORGANIC FILM ON CONCRETE SURFACE

BACKGROUND OF THE INVENTION

1. Field of the Invention

The present invention relates to a method and a device for detecting a pinhole in an organic film (or a resin lining) coating a concrete surface to protect it.

2. Description of the Prior Art

Buildings or structures of concrete (as will be shortly referred to as the "concrete structures") are employed in various fields because they are excellent in strength and workability. However, the concrete per se is degraded by the aging chemical changes due to the peripheral circumstances or by the changes in the using circumstances due to the corrosion of its reinforcement.

In order to prevent such aging degradation, there has been adopted the resin lining technique, by which the surface of a concrete structure is coated with an organic film composed mainly of a synthetic resin. This resin lining shields the concrete surface from the various liquids or gases in the peripheral circumstance, to protect the concrete structure. This obliges the resin lining (or film) to coat the whole surface of the structure reliably. This makes it necessary to manage the working so that no incomplete coating face may be formed all over the surface of the structure. It is also necessary to inspect whether or not the worked structure surface has an incomplete portion.

A relatively large defect such as the separation of or a large hole in the lining at the film on the concrete structure can be visually confirmed. In the resin film, however, there may be left either a void which is the trace of a small bubble formed when the resin lining was applied, or an invisibly small defect which is caused by external factors. This small defect implies a pinhole, a flaw and an extremely thin portion, all of which are usually called the "pinholes" (or commonly "holiday"). All of those larger or smaller defects will be called the "pinhole" in the present specification.

If the pinhole in the resin lining formed on the surface of the concrete structure is left unremedied, a liquid or gas will invade to the concrete surface through the through portion of the pinhole, to cause the degradation of the concrete. However, the pinhole includes an extremely small hole and is seriously difficult to inspect with the eyes, and a mere small recess may be misjudged as the pinhole. It is, therefore, necessary, to inspect the presence of the pinhole in the film either if necessary or periodically, and to remedy the defective portion.

In the prior art, there has already been used the discharge type pinhole inspector for inspecting the presence of the pinhole defect in the organic film which is applied to the surface of a metal such as a buried steel pipe, as will be described on its fundamental principle. As shown in FIG. 1A, a high voltage is applied between two conductive electrodes 100 and 101 which are held in the air with a clearance t, a high voltage is applied between the electrodes 100 and 101, and as the voltage difference is gradually increased, a discharging phenomenon or air dielectric breakdown is started between the leading end portions of the electrodes 100 and 101. If this voltage difference is further enlarged, there occurs a spark discharge. This spark discharge is stopped if an organic insulator plate 110 is inserted in this state between the electrodes 100 and 101, as shown in FIG. 1B. If a plate 112 having a small through pinhole 111 is inserted, however, as shown in FIG. 1C, the spark discharge or air dielectric breakdown occurs at the portion of the through pinhole 111, so that the pinhole detection can be made by detecting the change in the discharge current at this time.

FIG. 2 shows the behavior of the pinhole inspection of the prior art. In FIG. 2: reference letter A designates an organic film having an insulation; letter B a conductive parent material to which the organic film A is applied for its protection; and letter C a detecting brush electrode which is attached to the leading end of a probe for the inspecting operation and which has a brush of a number of fine brass wires. Letter E designates a pinhole inspector which is constructed to include a high-voltage generating portion, a high-voltage outputting connection portion, a discharge-current detecting portion, an informing drive portion such as a buzzer or lamp, an operating portion for controlling those individual portions, and a power source portion. Letter D designates a cord, as called the "earth cord", which is connected at its one end with the pinhole inspector E and is equipped at its other end with a clip or the like and connected with the parent material B. Here, the clip is connected with the parent material B. Letter G designates the so-called "probe cord", which is connected at its one end with the pinhole inspector E and at its other with the detecting brush electrode C. On the other hand, letter F designates a pinhole defect which is made in the organic film A.

In the above construction, the pinhole inspector E is controlled to apply the high voltage between the detecting brush electrode C and the parent material B and to slide the detecting brush electrode C on the surface of the organic film A. When the detecting brush electrode C is moved to pass over the pinhole defect F, there occurs the spark discharge, as has been described in connection with the fundamental principle. This discharge current is detected by the discharge current detecting portion of the pinhole inspector E so that the decision result is outputted. This output sounds the buzzer or flashes the lamp to inform the presence of the pinhole.

SUMMARY OF THE INVENTION

The present invention has an object to provide a method and a device for inspecting a pinhole in an organic film on a concrete surface, which is enabled to evaluate the presence the pinhole reliably in the organic film on the concrete surface, by applying the principle of a pinhole detector according to the discharge phenomenon and by detecting the conductivity of the concrete in advance.

In order to achieve the above-specified object, according to the present invention, there are provided: measuring means for evaluating the conductivity of the concrete which has an organic film formed on its surface; a pinhole inspector for detecting whether or not a pinhole is present in the organic film when it is decided by the measuring means that the concrete has the conductivity; and a method for detecting the presence of a pinhole reliably in the organic film on the concrete surface.

The measuring means is characterized by grasping and evaluating the specific dielectric constant of the concrete indirectly from the surface layer of the organic film formed on the concrete surface, without breaking the organic film to expose the concrete surface to the outside. Moreover, the pinhole inspector is characterized by comprising: a probe; an earth electrode; a power source for applying a high-voltage signal between the earth electrode and the probe; and a highly sensitive detector. The earth electrode is either a metallic portion such as reinforce in the concrete body or a conductive pad which can be fixed on the concrete body.

BRIEF DESCRIPTION OF THE DRAWINGS

In the accompanying drawings:

FIGS. 1A, 1B and 1C are diagrams for explaining the fundamental principle of a pinhole inspector of the prior art;

FIG. 2 is a construction diagram showing the behavior of a pinhole inspection of the prior art;

DESCRIPTION OF THE PREFERRED EMBODIMENTS

Figure 3:
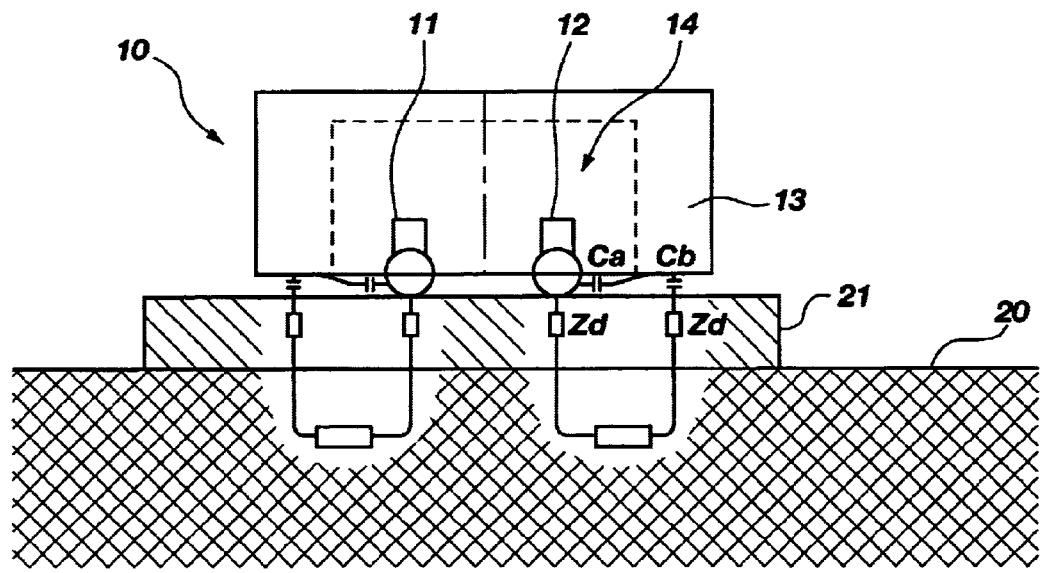
FIG. 3 is a sectional diagram showing the behavior of a measurement, as employed in the invention, for evaluating the conductivity of concrete.

The present invention makes a method possible for detecting a pinhole in an organic film on concrete by devising and applying the aforementioned fundamental principle of the pinhole detection. The concrete is inherently different from metals, and it has allowability for an electric current to flow through the concrete body, depending upon its state. For example, the concrete in an absolutely dry state (as left at 105° C. for 8 hours) has an extremely high impedance, and the concrete in a wet state (as left in water for seven days) has a low impedance in electric characteristics equivalent to those of water.

Here, the flowability of electricity (or current) of the concrete below the organic film is defined by terms "concrete conductivity", and the concrete is examined on how much water or conductive impurity it contains and on how much dielectric substance it contains. Moreover, the conductivity of the absolutely dry concrete will be defined by a numerical value "0", and the conductivity of the wet concrete will be defined by a numerical value "100". The ordinary concrete is within the conductivity values of "0 to 100", and a device for evaluating the flowability of electricity (or current) based on the degree of the water included in the concrete will be called a "conductivity indicator". Before an execution of the pinhole inspection of the organic film of the concrete, the numerical value of the evaluation of the conductivity of the concrete body is collated with an empirical data table (refer to FIG. 9) to decide whether or not the organic film can be inspected. If possible, the pinhole inspecting work is performed at a next step. The pinhole inspector to be used at this time is an inspector which is improved from a metal inspector for a metallic parent material having a resistivity of $(1 \text{ to } 100) \times 10^{-8} \Omega \cdot m$ to an inspector for a concrete parent material having a resistivity no more than $1 \times 10^7 \Omega \cdot m$.

By thus combining the conductivity indicator and the concrete pinhole inspector, it is possible to inspect the concrete surface film pinhole. However, the aforementioned method cannot be used in the place where it has been decided that the inspection cannot be made. However, no practical trouble occurs because the absolutely dry concrete is made at an extremely limited place.

The general characteristics of concrete will be described before the detailed description of the embodiment of the present invention is made with reference to the accompanying drawings.

Although the concrete is generally deemed as an insulation, but a number of fine clearances called capillary cavities are formed in the actual concrete between the aggregate (e.g., sand) and the cement particles or between the cement particles themselves. In the drying procedure after the kneading of the concrete, most of water content will diffuse in the cement particles in the hydration or will evaporate through the fine clearances. However, the water having wetting the surface of the cement particle or aggregate resides so long as the concrete is not heated. This residual water is made electrolyte with the alkalinity fed from the cement.

The portion, in which such fine clearances continue, is an electric resistor having a resistance and acts, if discontinuous, as a capacitor (or capacitance) because the discontinuity has a small volume. In other words, the concrete is electrically thought as a fine aggregate of "resistor+capacitor" to allow a DC current or AC current to flow therethrough. Although the concrete is a substance having a high impedance, therefore, it is hardly in the absolutely dry state, and most ordinary structures of the concrete have a resistivity no more than $1 \times 10^7 \Omega \cdot m$. This makes it possible to detect the pinhole of the organic film on the concrete surface if a detector packaged in the inspector is made highly sensitive.

In the present invention, therefore, the conductivity (or resistance or specific dielectric constant) of the concrete is evaluated at first, and the existence of the pinhole in the organic film on the concrete is detected when a predetermined condition is cleared. The principle for evaluating the conductivity of the concrete will be described in the following.

Figure 4:
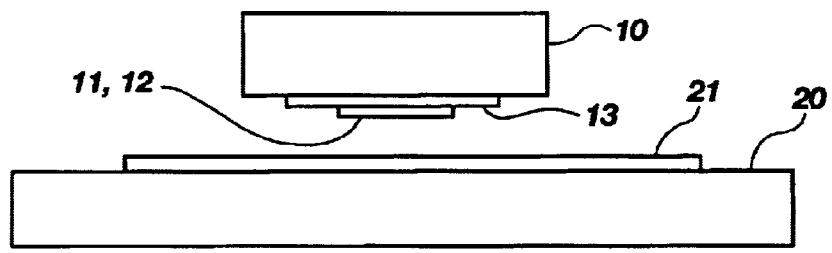
FIG. 4 is a side elevation showing the behavior of the measurement for evaluating the concrete conductivity.
Figure 5:
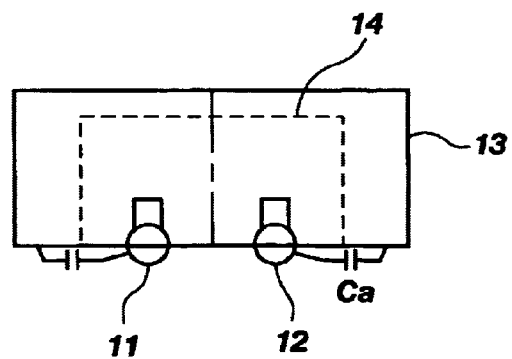
FIG. 5 is a side elevation of measurement means.
Figure 6:
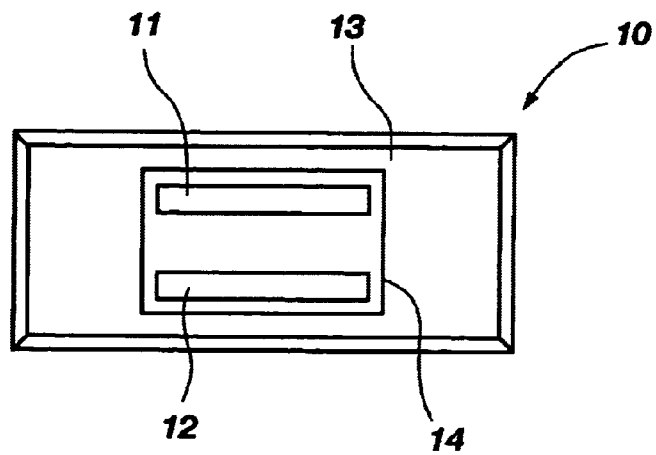
FIG. 6 is a bottom view of the measurement means.

FIG. 3 presents a sectional structure showing the behavior in which the conductivity of a concrete body 20 is measured by measuring means (or a conductivity evaluation unit) 10. With the surface of an organic film 21 coating the surface of the concrete body 20, there contact a pair of contact electrodes 11 and 12 which are arranged at a lower portion of the measuring means 10. FIG. 4 presents a side elevation of the structure and shows the case in which the contact electrodes. 11 and 12 are out of contact with the surface of the organic film 21. The structure of the measuring means 10 is made, as shown in FIGS. 5 and 6, such that an electrode 13 is mounted in a rectangular shape on the bottom center of the body of the measuring means 10 and such that the contact electrodes 11 and 12 are arranged in two parallel elongated shapes on the bottom face of the electrode 13 through an insulating member 14. In short, the contact electrodes 11 and 12 and the electrode 13 are electrically insulated through the insulating member 14. Here, the electrode 13 is not in contact with but in the vicinity (of 1.7 mm, for example) of the organic film 21.

Figure 7:
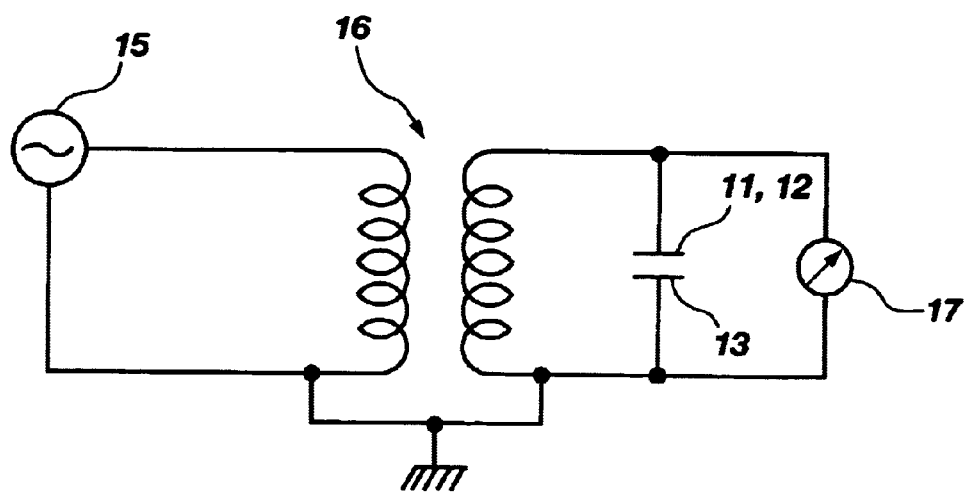
FIG. 7 is a connection diagram showing an example of the internal construction of the measurement means.

On the other hand, the measuring means 10 is internally constructed, as shown in FIG. 7, to accommodate a high-frequency oscillator 15, with which there is connected a transformer 16 for constructing a tuning circuit for the oscillation of the high-frequency oscillator 15. This high-frequency oscillator 15 oscillates and outputs a sinusoidal high-frequency signal having a frequency of 1 MHz to 10 MHz and an output voltage of about 10 to 20 V. The transformer 16 is connected at its output terminals with the contact electrodes 11 and 12 and the electrode 13 and is equipped with a current detector 17 for detecting a current change.

The electrode 13 and the contact electrodes 11 and 12 are coupled through a stray capacitance (or floating electrostatic capacitance) Cs when the body is in the air. A high-frequency voltage of 1 MHz or higher is applied between those two poles so that the packaged tuning circuit, as shown in FIG. 7, is in a tuned oscillatory state at an amplitude Vfs at a constant level. When the contact electrodes 11 and 12 are made in this state to contact with the organic film 21, there are added to the stray capacitance Cs a capacitance (Cb+Cb), an impedance (Zd+Zd) and an impedance (Zx+Zx), as shown in FIG. 3, so that the turned oscillatory state changes. Since the voltage also changes, therefore, this voltage change can be extracted to convert the impedance Zx, i.e, the impedance of the concrete together with the thickness of the organic film 21 into a numerical value indicating the conductivity or electric flowability.

Figure 8:
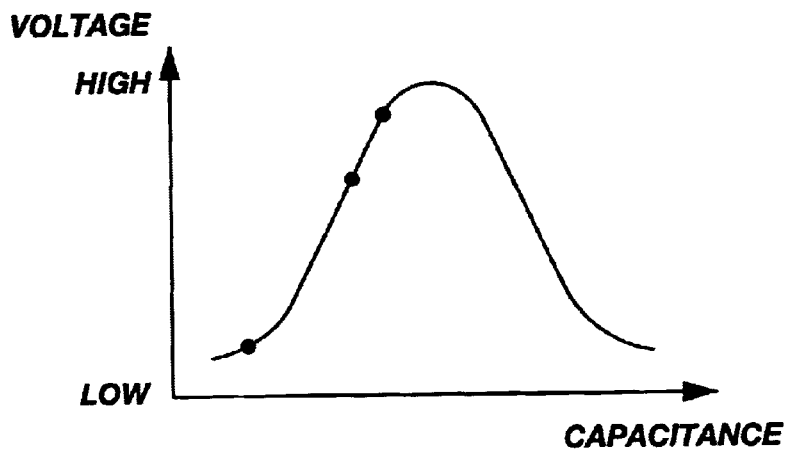
FIG. 8 is a characteristic diagram illustrating a relation between a capacitance and a voltage.

As described above, the contact electrodes 11 and 12 of the measuring means 10 are brought into contact with the surface of the organic film 21, and the high-frequency signal of 1 MHz to 10 MHz is oscillated from the high-frequency oscillator 15 so that the high-frequency signal, as tuned by the transformer 16, Is fed between the contact electrodes 11 and 12 and the electrode 13. As a result, the specific dielectric constant of the base body or concrete body 20 can be indirectly detected from the surface layer of the organic film 21 without breaking the organic film 21, as formed on the surface of the concrete body 20, to expose the surface of the concrete body 20 to the outside. As a result, the conductivity of the concrete body 20 can be evaluated from the correlation between the specific dielectric constant and the water content, as measured in advance, and from the correlation between the water content and the electric resistance. FIG. 8 is a characteristic diagram illustrating a relation between the capacitance and the voltage for the concrete.

When a DC resistance portion is to be measured on the actual concrete, the aqueous solution containing the alkalinity changes electrochemically so that the measured value drastically changes with the lapse of time. When the specific dielectric constant by the high-frequency is measured in the aforementioned manner, on the other hand, the measured value is stabilized by the effect of the capacitor portion in the concrete and is compatible with the facility of the discharge by the pinhole inspector. This implies that the measurement of the specific dielectric constant by the high-frequency is advantageous for the conductivity evaluation of the concrete.

The aforementioned specific dielectric constant is usually composed of "the water content in the concrete+the lining film+the concrete aggregate". Of the individual specific dielectric constants, generally: the city water has a constant of "80"; the resin film has a constant of "3 to 4"; and the concrete aggregate has a constant of about "5 to 6". Here, the aggregate contains finer aggregate (e.g., sand) and coarser aggregate (e.g., gravel or pebble). Thus, the specific dielectric constant of water has a far larger value than those of the remaining components so that the overall specific dielectric constant responds sensitively to the ratio of water content in the concrete. In the case of the concrete, it is widely known that the water content is the higher for the larger specific dielectric constant thereby to improve the conductivity the better. Depending upon the specific dielectric constant measured from over the lining film, therefore, it is possible to accurately decide whether or not the pinhole inspection is correct.

Figure 9:
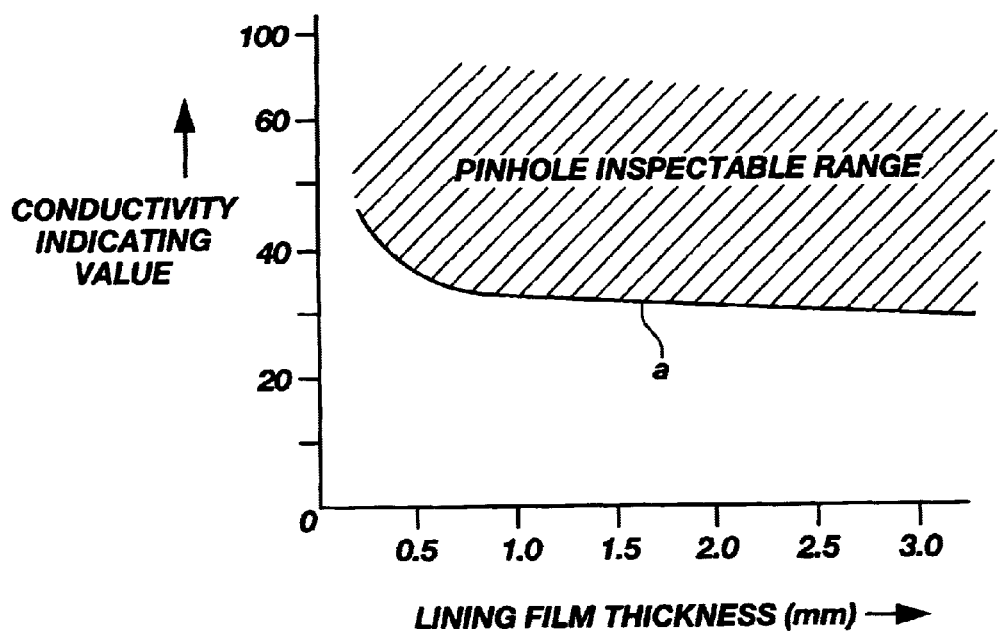
FIG. 9 is a characteristic diagram illustrating a pinhole inspectable range.

From the discussion thus far made, for example, an epoxy film is formed on the surface of the concrete, and the relation between the thickness of the film and the conductivity indicating value is considered to determine the boundary for which the pinhole inspection can be made, as illustrated in FIG. 9. In FIG. 9, the hatched portion over a boundary line a provides the conductible region. In the blank region having the conductivity indicating value below the boundary line a, the corresponding concrete lacks the conductivity necessary for the pinhole inspection.

When there is obtained the result that the concrete body 20 is conductive, that is, when the conductivity indicating value measured by the measuring means 10 belongs to the hatched region over the boundary line a of FIG. 9, the work to detect the pinhole is performed at the next step.

Figure 10:
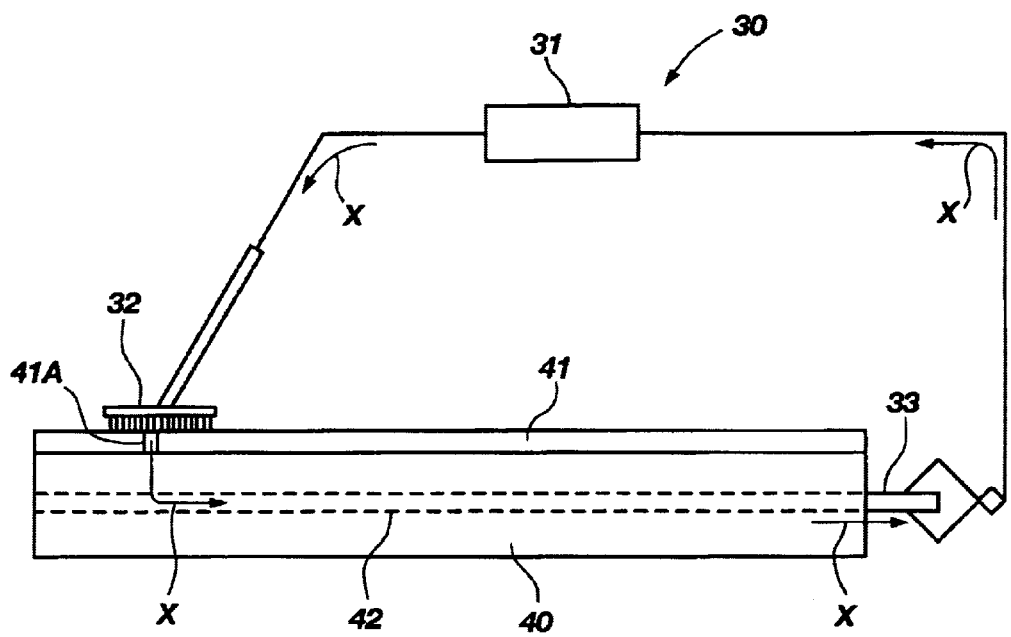
FIG. 10 is a construction diagram showing one embodiment of a pinhole inspector according to the invention.

FIG. 10 is a schematic construction diagram showing one embodiment of a pinhole inspector 30 according to the present invention. This pinhole inspector 30 inspects whether or not an organic film 41 coating the surface of a concrete body 40 has a pinhole. An inspector 31 having a high-voltage power source (at 5 KV to 15 KV, for example, if the organic film 41 has a thickness within 3 mm) packaged therein is connected at its one end with a probe 32 made of a brush electrode to contact with the surface of the organic film 41 and an other end is connected with an earthing reinforcement 33.

In the concrete body 40, reinforcement 42 never fail to be buried so as to retain a strength. These reinforcements 42 are connected by the not-shown placing method so that they are electrically at the same potential. Since the reinforcement protruded from the face of the concrete body 40 is often welded and is connected to the buried ones such as the handrail, the scaffold or the ladder, and the potential is equivalent to the reinforcement 33. Therefore, the ground (or earth) potential is taken by making use of the metallic portion.

Next, in the hatched region where the concrete is conductive as shown in FIG. 9, it is then sufficient to move the probe 32 over the surface of the organic film 41. When the organic film 41 has a pinhole 41A, the spark discharge is caused by occurring the dielectric breakdown in the gap of the pinhole 41A. The discharge electric current at this time flows, as indicated by arrow X in FIG. 10. This spark discharge is electrically detected by the inspector 31 to inform the presence of the pinhole 41A by making a buzzer sound or flashing a lamp. Although not shown, the circuit is cut at the instance of the discharge to prevent the damage of the organic film 41, as might otherwise be caused if the discharge continued, and to improve the safety against the electric shock. In the actions thus far described, the description has been made on the DC current but likewise applies to the AC current.

Figure 11:
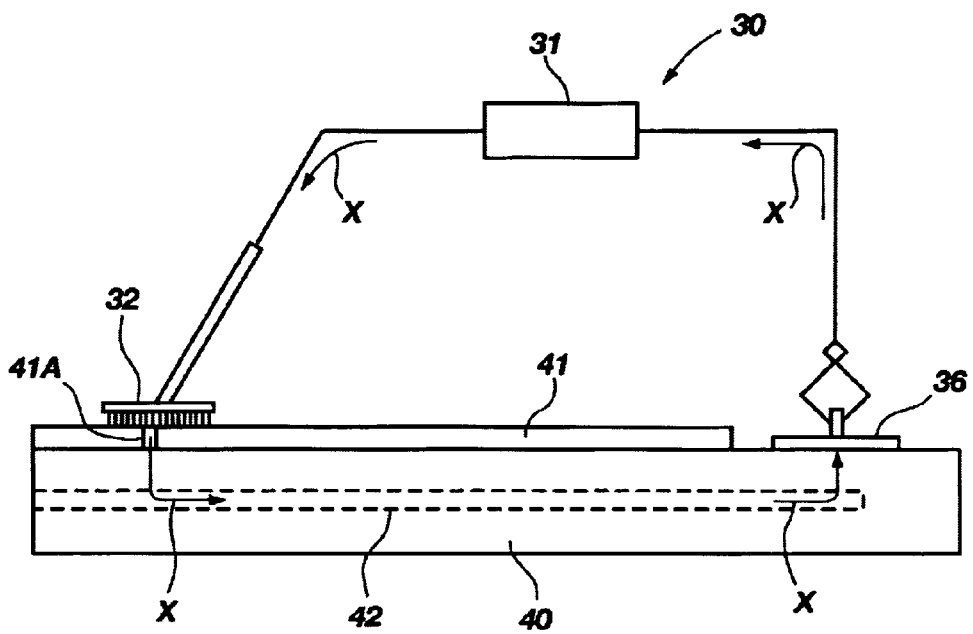
FIG. 11 is a construction diagram showing another embodiment of the pinhole inspector according to the present invention.

FIG. 11 shows another embodiment of the earthing connections, and the common reference numerals are employed to designate the same components as those of FIG. 10. In this embodiment, a well-known plate-shaped conductive pad 36 (an effective area of 15 $cm^2$ or more and an electric contact resistance of 30KΩ or more and is made so adhesive), as commercially available., is adhered and fixed in close contact to the concrete body 40 which is not coated with the organic film 41. Alternatively, the earthing may be taken either from the anchor bolts to be employed for fixing the device facilities on the concrete body 40 or from the risers of metallic piping for service water or electric power. As the probe 32 is moved in this state over the organic film 41, the flow of the electric current when the organic film 41 has the pinhole 41A is in the sequence of the pinhole 41A→the concrete body 40→the buried reinforcement 42→the concrete body 40→conductive pad 36 (or metallic member)→the inspector 31. The electric current flows in the concrete body 40 through the portion of the pinhole 41A and the portion of the conductive pad 36 (metallic member). However, since the contact resistance is small, there is no influence to the detection of the discharge current.

Here, in the actions thus far described, the description has been made on the DC current but likewise applies to the AC current.

As has been described hereinbefore, according to the present invention, there is achieved an advantage that an ordinary person having no technique or experience is enabled to simply inspect whether or not the organic film 41 coating the concrete surface has a pinhole, by evaluating the conductivity of the concrete in advance.

What is claimed is:

1. A method for detecting a pinhole in an organic film on a concrete surface, comprising:

an evaluation step of evaluating the conductivity of concrete having the organic film formed on its surface; and an inspection step of inspecting whether or not a pinhole is present in said organic film, when the conductivity value of the concrete is revealed by said evaluation step to be no less than a predetermined value, which changes with the thickness of said organic film; and wherein said evaluation step grasps and evaluates the specific dielectric constant of the concrete indirectly from the surface layer of the organic film formed on the surface, without breaking the organic film to expose the concrete surface to the outside, and said inspection step is based on the electric fluctuation caused by a discharge.

2. A pinhole detecting method in an organic film on a concrete surface according to claim 1, wherein a plus electrode is brought into contact with said organic film so that a high-frequency signal is applied between said plus electrode and a minus electrode which is insulated from said plus electrode but is close to said organic film.

3. A pinhole detecting method in an organic film on a concrete surface according to claim 1, wherein said discharge is generated when the pinhole is present, by applying a high voltage between a probe and an earth electrode and by moving said probe along the surface of said organic film.

4. A pinhole detecting method in an organic film on a concrete surface according to claim 3, wherein the application of said high voltage is blocked at the instant when said discharge occurs.

* * * * *